US008460328B2

(12) United States Patent
Piferi

(10) Patent No.: US 8,460,328 B2
(45) Date of Patent: Jun. 11, 2013

(54) SURGICAL MARKING TOOLS AND METHODS FOR MARKING A PATIENT

(75) Inventor: Peter Piferi, Orange, CA (US)

(73) Assignee: MRI Interventions, Inc., Memphis, TN (US)

( * ) Notice: Subject to any disclaimer, the term of this patent is extended or adjusted under 35 U.S.C. 154(b) by 0 days.

(21) Appl. No.: 13/421,344

(22) Filed: Mar. 15, 2012

(65) Prior Publication Data

US 2012/0172878 A1  Jul. 5, 2012

Related U.S. Application Data

(62) Division of application No. 12/236,615, filed on Sep. 24, 2008, now Pat. No. 8,157,828.

(60) Provisional application No. 61/041,500, filed on Apr. 1, 2008, provisional application No. 60/974,821, filed on Sep. 24, 2007.

(51) Int. Cl.
*A61B 17/14* (2006.01)

(52) U.S. Cl.
USPC ........................................ 606/180; 600/411

(58) Field of Classification Search
USPC .............. 606/54, 60, 130, 104, 180; 600/411, 600/426; 81/438, 453
See application file for complete search history.

(56) References Cited

U.S. PATENT DOCUMENTS

| 2,775,276 | A | 12/1956 | Rossner | |
|---|---|---|---|---|
| 4,763,548 | A | 8/1988 | Leibinger et al. | 81/453 |
| 5,643,269 | A | 7/1997 | Härle | |
| 5,925,048 | A | 7/1999 | Ahmad et al. | |
| 6,368,330 | B1 | 4/2002 | Hynes et al. | |
| 6,610,067 | B2 * | 8/2003 | Tallarida et al. | 606/102 |
| 6,949,105 | B2 | 9/2005 | Bryan et al. | 606/130 |
| 2002/0193799 | A1 | 12/2002 | Chappuis et al. | |
| 2005/0070907 | A1 | 3/2005 | Abernathie | |
| 2007/0106305 | A1 | 5/2007 | Kao et al. | 606/130 |
| 2007/0162018 | A1 | 7/2007 | Jensen et al. | |

FOREIGN PATENT DOCUMENTS

| DE | 296 11 140 U1 | 9/1996 |
|---|---|---|
| EP | 0 508 849 A1 | 10/1992 |
| WO | WO 2005/084572 A2 | 9/2005 |
| WO | WO 2005/084572 A3 | 9/2005 |

OTHER PUBLICATIONS

"Standard Specification and Test Methods for Metallic Medical Bone Screws[1] ", ASTM International, Designation: F 543-02[E1] ; www.astm.org, Last downloaded Sep. 10, 2008 (Jun. 2002).
International Search Report and Written Opinion (16 pages) corresponding to International Application No. PCT/US2008/011083; Mailing Date: Dec. 22, 2008.

* cited by examiner

*Primary Examiner* — Victor Nguyen
(74) *Attorney, Agent, or Firm* — Myers Bigel Sibley & Sajovec, PA

(57) ABSTRACT

A surgical marking tool for marking a location on a patient includes a cutting head and a handle. The cutting head includes a screw thread. The handle is coupled to the cutting head to rotate the cutting head. The screw thread is configured to progressively embed in the patient to mark the location when the cutting head is placed in contact with the patient and rotated with respect to the patient using the handle.

16 Claims, 5 Drawing Sheets

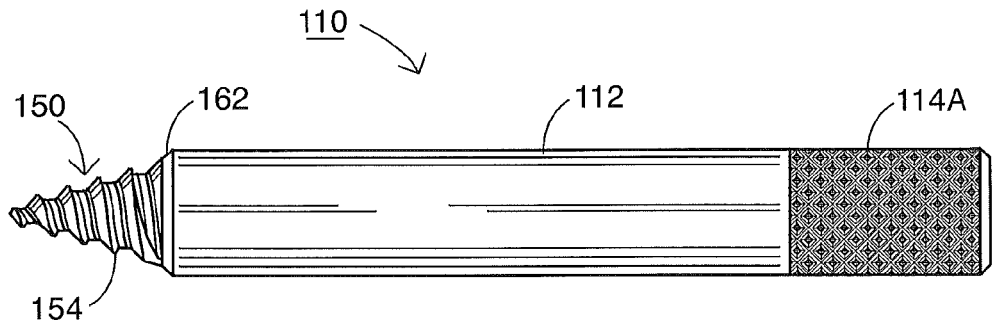
FIG. 4
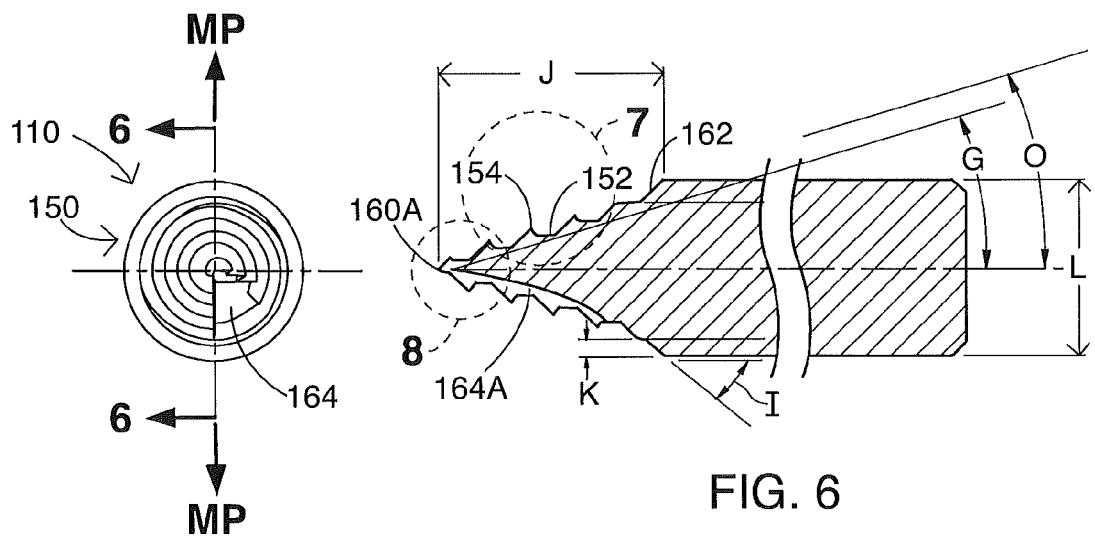
FIG. 5
FIG. 6
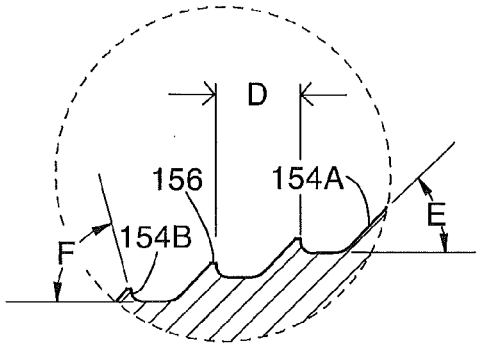
FIG. 7
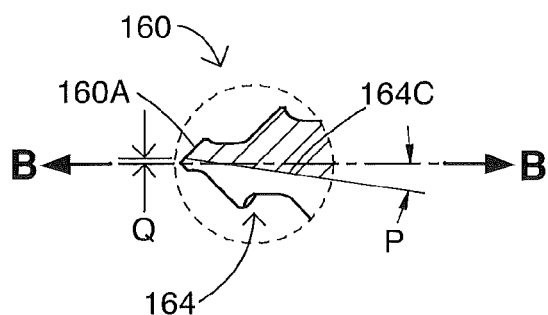
FIG. 8

SURGICAL MARKING TOOLS AND METHODS FOR MARKING A PATIENT

RELATED APPLICATION(S)

The present application is a divisional patent application of and claims priority from U.S. patent application Ser. No. 12/236,615, filed Sep. 24, 2008 now U.S. Pat. No. 8,157,828, which claims the benefit of U.S. Provisional Patent Application No. 61/041,500, filed Apr. 1, 2008, and U.S. Provisional Patent Application No. 60/974,821, filed Sep. 24, 2007, the disclosures of which are incorporated herein by reference in their entireties.

FIELD OF THE INVENTION

The present invention relates to medical devices and, more particularly, tools and methods for marking a patient.

BACKGROUND OF THE INVENTION

It is often desired to mark a patient to designate a location for incision or entry into the patient with a medical interventional device. For example, a physician may wish to mark a location on a patient's head to indicate the desired placement of a burr hole.

SUMMARY OF THE INVENTION

According to embodiments of the present invention, a surgical marking tool for marking a location on a patient includes a cutting head and a handle. The cutting head includes a screw thread. The handle is coupled to the cutting head to rotate the cutting head. The screw thread is configured to progressively embed in the patient to mark the location when the cutting head is placed in contact with the patient and rotated with respect to the patient using the handle.

In some embodiments, the screw thread includes a self tapping screw thread. The marking tool is a burr hole marking tool and the self tapping screw thread is configured to self tap into a human skull. The cutting head can have a sharp leading end section configured to easily pierce through the patient's scalp. In some embodiments, the cutting head has a lead end and a limiter feature spaced apart a distance from the lead end, and an axial boring length extending from the lead end to a proximal end of the limiter feature is less than a thickness of the patient's skull.

According to some embodiments, the handle includes first and second handle members that cooperate and are rotatable with respect to one another, and the cutting head is affixed to the first handle member for rotation therewith. In some embodiments, the first handle member is a lower handle member and the second handle member is an upper handle member, and the upper handle member is configured and positioned to be held by a user's hand while the user rotates the cutting head using the lower handle member. The upper handle member may have an upper end portion with a bulbous shape. The lower handle member can include flutes.

The marking tool can be constructed entirely of MRI-compatible material or materials.

According to method embodiments of the present invention, a method for marking a location on a patient includes: providing a surgical marking tool including a cutting head having a screw thread; and placing the cutting head in contact with the patient and rotating the cutting head with respect to the patient to progressively embed the screw thread in the patient to mark the location.

According to some embodiments, the screw thread includes a self tapping screw thread, and the method includes cutting into the patient using the self tapping screw thread.

In some embodiments, placing the marking tool in contact with the patient and rotating the marking tool with respect to the patient includes progressively embedding the screw thread into a skull of the patient to mark the location in the skull. The method can include piercing through the scalp of the patient with a sharp leading end section of the cutting head. In some embodiments, the screw thread includes a self tapping screw thread, and the method includes cutting into the patient's skull using the self tapping screw thread. According to some embodiments, the method includes embedding the cutting head into the patient's skull only to a maximum depth less than the thickness of the skull, and thereafter removing the cutting head from the skull. The method can further include forming a burr hole in the patient's skull proximate the marked location after the marking tool is removed.

The marking tool may include a handle coupled to the cutting head to rotate the cutting head. In some embodiments, the handle includes first and second handle members that are rotatable with respect to one another, the cutting head is affixed to the first handle member, and rotating the cutting head with respect to the patient includes rotating the first handle member with respect to the second handle member. According to some embodiments, the first handle member is a lower handle member and the second handle member is an upper handle member, and the method includes holding the upper handle member in a user's hand and simultaneously rotating the cutting head using the first handle member.

According to some embodiments, the marking tool is constructed entirely of MRI-compatible material or materials, and the steps of placing the cutting head in contact with the patient and rotating the cutting head with respect to the patient are executed in or adjacent a magnet of an MRI scanner.

The method may include counter-rotating the cutting head with respect to the patient to progressively remove the cutting head from the patient.

According to further embodiments of the present invention, a surgical kit for an MRI-guided interventional surgery on a patient includes a surgical marking tool and sterile packaging containing the marking tool. The marking tool includes a cutting head and a handle. The cutting head includes a screw thread. The handle is coupled to the cutting head to rotate the cutting head. The screw thread is configured to progressively embed in the patient to mark a location on the patient when the cutting head is placed in contact with the patient and rotated with respect to the patient using the handle. The marking tool is constructed entirely of MRI-compatible material or materials.

Further features, advantages and details of the present invention will be appreciated by those of ordinary skill in the art from a reading of the figures and the detailed description of the preferred embodiments that follow, such description being merely illustrative of the present invention.

BRIEF DESCRIPTION OF THE DRAWINGS

FIG. 4 is a side elevational view of a driver shank forming a part of the marking tool of FIG. 1.

FIG. 5 is a front plan view of the driver shank of FIG. 4.

FIG. 6 is a cross-sectional view of the driver shank of FIG. 4 taken along the line 6-6 of FIG. 5.

FIG. 7 is an enlarged view of Detail 7 of FIG. 6.

FIG. 8 is an enlarged view of Detail 8 of FIG. 6.

DETAILED DESCRIPTION OF EMBODIMENTS OF THE INVENTION

Figure 1:
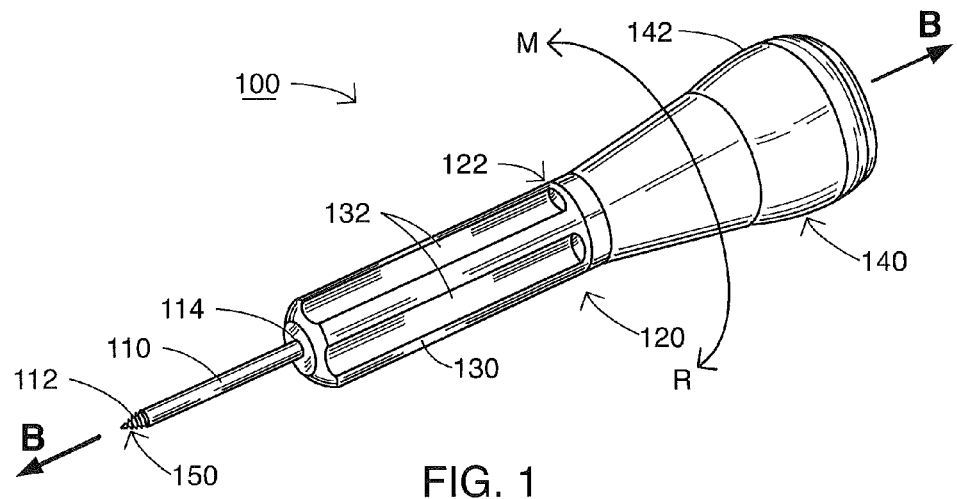
FIG. 1 is a front, perspective view of a surgical marking tool according to embodiments of the present invention.
Figure 2:
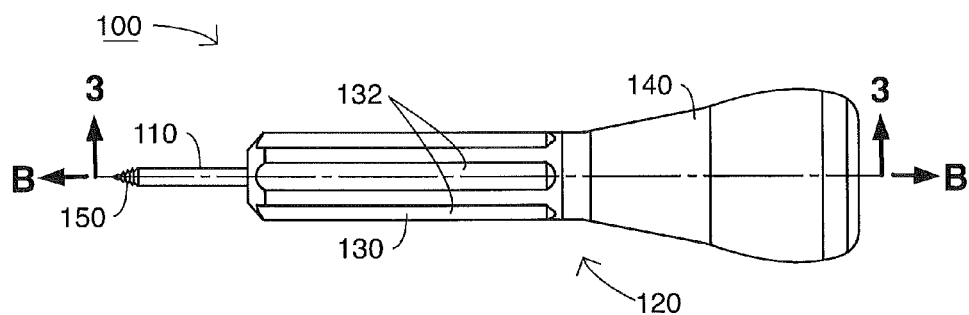
FIG. 2 is a side elevational view of the marking tool of FIG. 1.

The present invention now will be described more fully hereinafter with reference to the accompanying drawings, in which illustrative embodiments of the invention are shown. In the drawings, the relative sizes of regions or features may be exaggerated for clarity. This invention may, however, be embodied in many different forms and should not be construed as limited to the embodiments set forth herein; rather, these embodiments are provided so that this disclosure will be thorough and complete, and will fully convey the scope of the invention to those skilled in the art.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90° or at other orientations) and the spatially relative descriptors used herein interpreted accordingly.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

According to embodiments of the present invention, surgical marking tools and methods for using the same are provided for marking a location on a patient for surgical entry, for example. According to some embodiments, the marking tools and methods are used or usable to mark a patient's skull. Such marking may be employed to indicate to a physician a designated location for entry into the patient (for example, through the patient's skull). According to some embodiments, a mark formed by the marking tool is used as a reference point (for example, a centering point) for subsequent formation of a burr hole or other access port in the patient.

With reference to FIGS. 1-8, a marking tool 100 according to embodiments of the present invention is shown therein. The marking tool 100 includes a driver shank 110, a handle assembly 120, and a cutting head 150.

The handle assembly 120 can be ergonomically configured, for example, as shown. The handle assembly 120 includes a distal or lower handle member 130 and a proximal or upper handle member 140. The lower handle member 130 can be coupled to the upper handle member 140 to permit rotation relative to the upper handle member 140 in each of a clockwise direction M and a counterclockwise direction R (as viewed from the upper handle member end) about a driver axis B-B and at an interface 122. According to some embodiments, the relative axial positions of the lower handle member 130 and the upper handle member 140 are fixed.

The lower handle member 130 and the upper handle member 140 may be rotatably coupled by any suitable mechanism or means. According to some embodiments and with reference to FIG. 3, the lower handle member 130 includes an upper extension 134 that is rotatably received in a bore 144 (optionally, and as shown, a through bore) of the upper handle member 140. As shown, a bolt 102 extends through a bearing washer 104 and is threadedly secured in a fastener bore 130A of the extension 134. The lower handle member 130 is thereby axially captured in the through bore 144 by a shoulder 136 of the lower handle member 130 and the bearing washer 104, which slidably engages a flange 146 of the upper handle member 140. According to other embodiments, the lower handle portion 130 may have one or more snap fit features in place of the bolt 102 to rotatably secure the lower handle member 130 to the upper handle member 140.

According to some embodiments and as illustrated, the lower handle member 130 is provided with ribs or flutes 132 to facilitate manipulation of the lower handle member 130 by the operator's fingers. According to some embodiments and as illustrated in FIG. 1, the upper handle member 140 includes an enlarged or bulb-shaped portion 142 on its upper end to facilitate the grip and manipulation of the upper handle member 140 by the operator's hand or palm.

Figure 3:
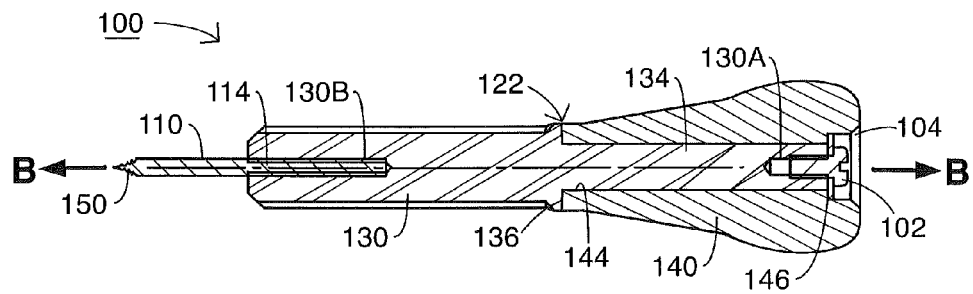
FIG. 3 is a cross-sectional view of the marking tool of FIG. 1 taken along the line 3-3 of FIG. 2.

Referring to FIG. 3, the driver shank 110 has a lower section 112 on which the cutting head 150 is affixed or integrally formed. An upper section 114 of the driver shank 110 is affixed to the lower handle member 130. According to some embodiments, the upper section 114 is received in a shank bore 130B in the lower handle member 130. The upper section 114 of the driver shank 110 may be securely held in the bore 130B by molding, adhesive, and/or knurling 114A (on the exterior of the upper section 114), for example, to prevent relative rotation between the driver shank 110 and the lower handle member 130. According to some embodiments, the upper section 114 may have a geometric shape that resists relative rotation between the upper section 114 and the lower handle member 130. In this manner, the driver shank 110 and the cutting head 150 are together rotatable relative to the upper handle member 140.

According to some embodiments, the cutting head 150 includes a threaded screw shank. According to some embodiments, the threaded screw shank is a self-tapping or self-drilling screw structure. According to some embodiments, the cutting head 150 is configured as a self-tapping bone screw configured to make a controlled and visually detectable hole in bone without undue force against the scalp/skull.

A cutting head 150 according to embodiments of the present invention is shown in enlarged detail in FIGS. 4-8, wherein the cutting head 150 includes a tapered root or shank 152, a screw thread 154 helically wound about the shank 152 and having a crest 156 (FIG. 7), a leading end section 160 terminating in a leading tip or point 160A, a limiter feature or land 162 (FIGS. 4 and 6) opposite the tip 160A, and a cutting notch or flute 164 (FIGS. 6 and 8) formed in the leading end section 160.

According to some embodiments, the root 152 is uniformly tapered. According to some embodiments, the root 152 has a minor diameter half angle G (FIG. 6) in the range of from about 10 to 35 degrees.

According to some embodiments, the thread 154 is a generally V-shaped or U-shaped thread. According to some embodiments, the thread 154 has a substantially uniformly tapered major diameter. According to some embodiments, the taper half angle O (FIG. 6) of the major diameter is in the range of from about 10 to 35 degrees. According to some embodiments, the angle E (FIG. 7) of the leading flank 154A with respect to the minor diameter is less than the angle F of the trailing flank 154B with respect to the minor diameter. According to some embodiments, the leading flank angle E is in the range of from about 30 to 60 degrees, and the trailing flank angle F is in the range of from about 50 to 100 degrees. The relatively lesser angle of the leading flank reduces the wedge angle upon insertion and the relatively greater angle of the trailing flank can reduce pullout by maintaining the trailing flank more nearly parallel with the penetrated surface.

According to some embodiments, the pitch D (FIG. 7) of the thread 154 is substantially constant. According to some embodiments, the pitch D is in the range of from about 0.5 to 2 mm.

As shown in FIG. 6, the leading end section 160 can be generally conical. According to some embodiments, the thread 154 extends substantially fully to the tip 160A. However, according to other embodiments, a distal portion of the leading end section 160 may be sharp and nonthreaded (not shown).

The flute 164 (FIGS. 6 and 8) can define a bone chip collection pocket within the cutting head 150 to receive bone or other material through which the cutting head 150 is driven. As shown in FIG. 6, for example, the flute 164 defines a cutting face 164A having a sharp cutting edge 164B and an opposed inner edge 164C. According to some embodiments, the cutting face 164A extends fully to the tip 160A. According to some embodiments, the cutting face 164A is substantially coplanar with a mid-plane MP (FIG. 5) of the screw shank 152. According to some embodiments, the inner edge 164C extends transverse to and across the centerline B-B of the shank 152. According to some embodiments, an axis of the inner edge 164C crosses the centerline B-B (within the shank 152) and forms an angle P (FIG. 8) in the range of from about 0 to 60 degrees with respect to the centerline B-B. According to some embodiments, the inner edge 164C extends across the centerline B-B at the tip 160A a distance Q (FIG. 8) in the range of from about 0 to 0.5 mm.

According to some embodiments, the land 162 is non-threaded and tapers at a substantially steeper angle I (FIG. 6) than the angle G of the root 152. According to some embodiments, the angle I of the land 162 is in the range of from about 30 to 90 degrees.

According to some embodiments, the working or axial boring length J (FIG. 6) of the cutting head 150 (i.e., the lengthwise distance from the tip 160A to the proximal end of the land 162) is in the range of from about 2.5 to 7 mm and, according to some embodiments, in the range of from about 3 to 5 mm.

According to some embodiments, the outer diameter L (FIG. 6) of the land 162 is in the range of from about 2 to 6 mm. According to some embodiments, the width K of the land 162 is in the range of from about 0.5 to 1.5 mm.

According to some embodiments, the cutting head 150 complies with ASTM Standard F543-02 (Standard Specification and Test Methods for Metallic Medical Bone Screws), the disclosure of which is incorporated herein by reference.

The components of the marking tool 100 may be formed of any suitable biocompatible materials. According to some embodiments, the driver shank 110 and the cutting head 150 are formed of a metal such as titanium or stainless steel. According to some embodiments, the handle members 130, 140 are formed of a suitable polymeric material such as ABS or polycarbonate.

In some embodiments, the marking tool 100 comprises MRI-compatible material(s) and, according to some embodiments is constructed entirely of MRI-compatible material or materials. The term "MRI compatible" means that the so-called component(s) are safe for use in an MRI environment (e.g., in a high magnetic field of an MRI scanner) and are typically made of non-ferromagnetic MRI compatible material(s) suitable to reside and/or operate in a higher magnetic field environment. The term "high magnetic field" refers to field strengths above about 0.5 T, typically between 1.5 T and 10 T associated with MRI/MRS scanners.

Figure 9:
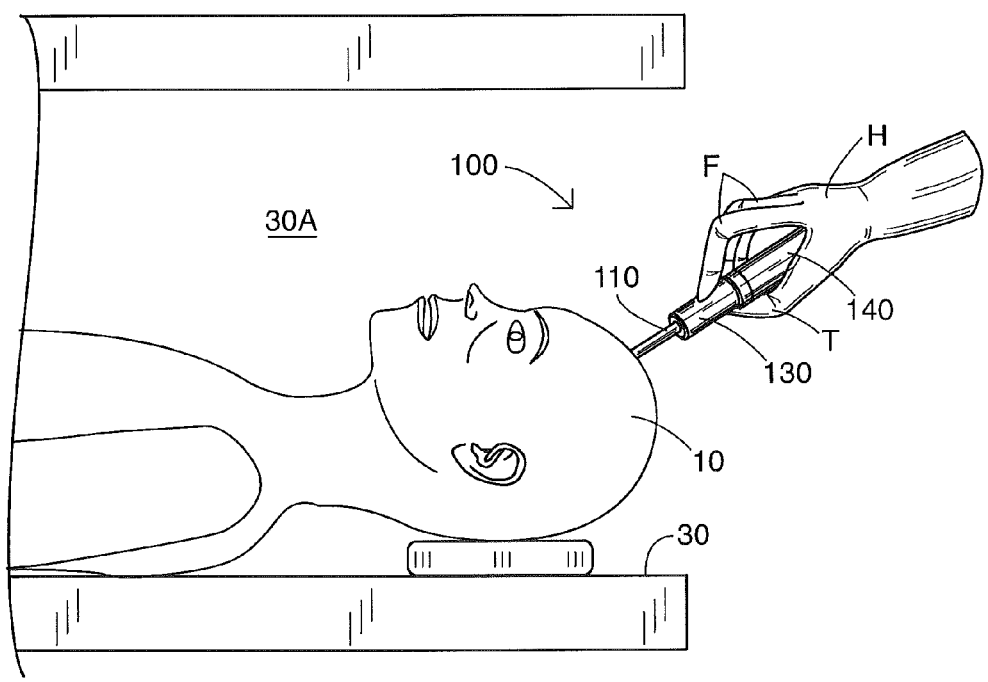
FIG. 9 is a schematic view of a patient in an MRI scanner being marked with the marking tool of FIG. 1.
Figure 10:
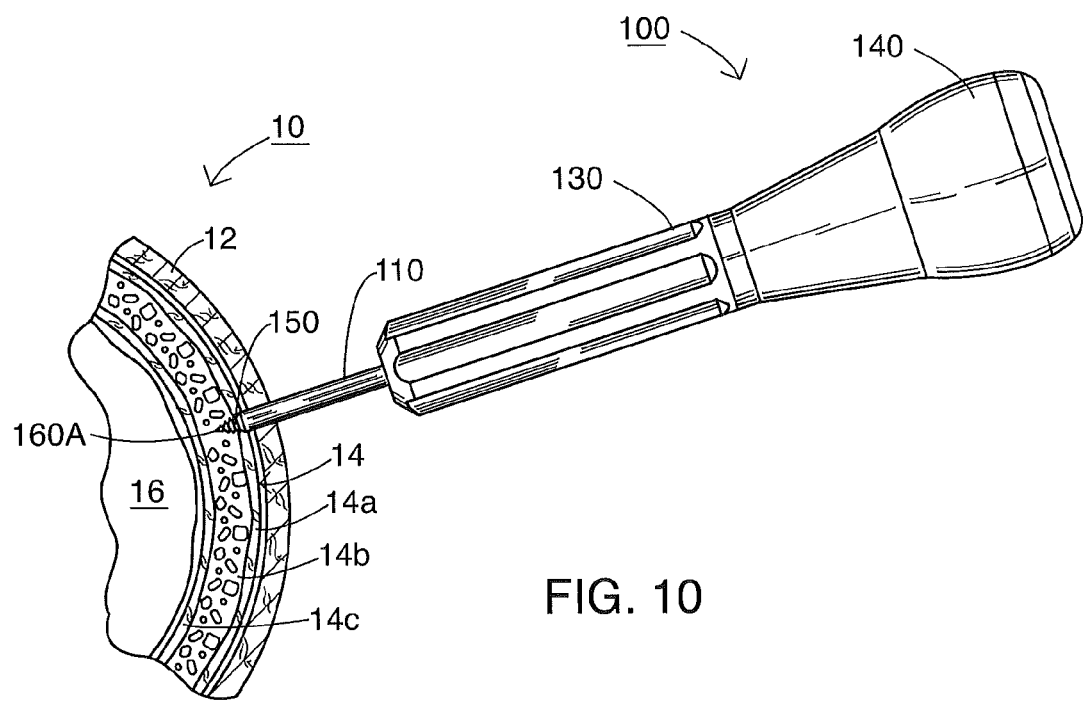
FIG. 10 is an enlarged, fragmentary view of the patient's head with the marking tool of FIG. 1 embedded therein.
Figure 11:
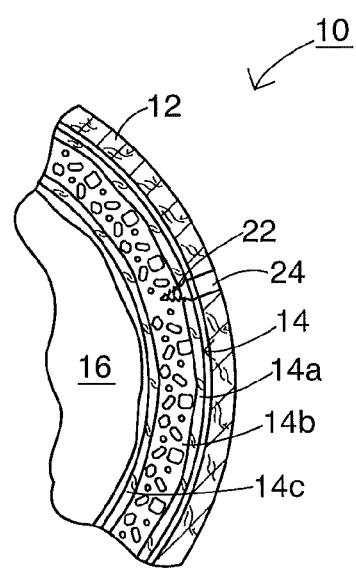
FIG. 11 is an enlarged, fragmentary view of the patient's head after being marked with the marking tool of FIG. 1.
Figure 12:
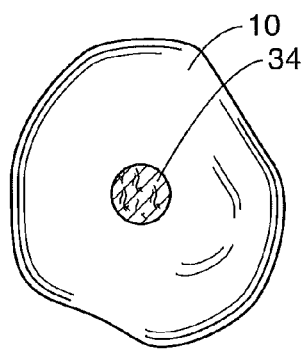
FIG. 12 is an enlarged view of the patient's head with a burr hole formed therein.
Figure 13:
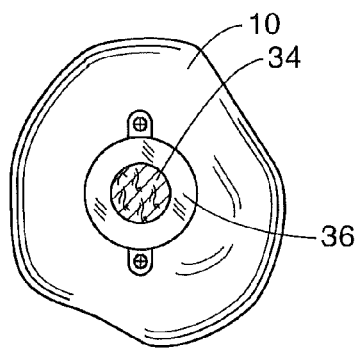
FIG. 13 is an enlarged view of the patient's head with a burr hole ring mounted thereon.

Operation and use of the marking tool 100 and methods according to embodiments of the present invention will be further described with reference to FIGS. 9-13. Referring to FIG. 10, a portion of a patient's head 10 is shown therein in schematic cross-section. The head 10 includes an outer skin (and other soft tissue) layer (referred to herein as the scalp) 12, a skull 14, and underlying brain tissue 16. The skull 14 includes an outer compact bone layer 14A, an inner compact bone layer 14C, and a spongy bone layer 14B between the compact bone layers 14A and 14C.

Initially, a location on the head 10 may be identified by a suitable technique and/or apparatus. This location may be suitably temporarily marked or designated. Once the desired location is determined, the operator can grasp the marking tool 100 such that the upper handle member 140 is held in the palm of the operator's hand H to stabilize the marking tool 100 (e.g., as shown in FIG. 9). The operator's fingers F and thumb T may rest on the lower handle member 130. The operator places the cutting head 150 in contact with the patient's head 10. The operator may press the cutting head 150 into the patient's head 10 such that the cutting head 150 penetrates through the skin 12 and may partially penetrate into the skull 14. More particularly, the sharp tip 160A and leading end section 160 easily pierce through the skin 12.

The operator then holds the marking tool 100 steady and simultaneously rotates the lower handle member 130 using his or her fingers F and thumb T to thereby rotate the cutting head 150 in the clockwise direction M. The operator may apply pressure along the axis B-B toward the skull 14 simultaneously with rotating the cutting head 150. In this manner, the self tapping screw thread 154 cuts into the skull 14 to progressively embed the cutting head 150 into the skull 14 as shown in FIG. 10. More particularly, the self tapping screw thread 154 initiates and cuts or forms a corresponding thread on the skull 14 as the cutting head 150 is rotated in the direction of the thread 154. The sharp crests 156 may minimize or reduce the torque required to penetrate, engage and self tap into both the soft tissue 12 and the skull 14.

According to some embodiments, the cutting head 150 is configured to limit the penetration distance N (FIG. 10) of the cutting head 150 (i.e., to the tip 160A) into the skull 14. The relatively steep and constant taper angle G of the cutting head 150 may prevent or substantially inhibit the user from rotatively driving or embedding the cutting head 150 into the skull 14 beyond the prescribed maximum permitted depth. The steep, threadless land 162 may also reduce the risk of over-penetration. According to some embodiments, the cutting head 150 is configured to permit the operator to screw the cutting head 150 through the scalp 12 and into the skull 14, but not fully through the thickness of the skull 14. According to some embodiments, the cutting head 150 is configured to permit the operator to screw the cutting head 150 through the scalp 12, through the outer compact bone layer 14A, and into the spongy bone layer 14B, but to prevent the operator from penetrating the inner compact bone layer 14C.

The operator may thereafter use his or her fingers F, T to rotate the lower handle member 130 in the counterclockwise direction R while holding the marking tool 100 steady via the upper handle member 140. In this manner, the screw thread 154 is unscrewed from the skull 14 and the cutting head 150 is thereby backed out of the skull 14. The operator may then remove the marking tool 100 fully from the patient 10.

A visually identifiable mark 20 will thereafter remain in the surface of the skull for the physician's visual reference. The mark 20 includes both a small threaded hole 22 in the skull layers 14A, 14B (but which does not extend into the brain) and an opening or hole 24 in the skin 12. According to some embodiments, the depth N of the mark 20 in the skull 14 will be between about 10 and 100 percent of the working length J of the cutting head 150.

The marking tool 100 according to embodiments of the present invention can thus be used to form a precisely positioned, readily visually detectable, persistent mark on the patient.

According to some embodiments, the marking procedure is executed with the patient's head in or adjacent a bore 30A of a high-field magnet of an MRI scanner 30 as shown in FIG. 9 (can be open bore or closed bore magnets).

A burr hole 34 (FIG. 12) can thereafter be formed in the head 10 at the location of the mark 20 using any suitable technique or device. For example, the burr hole 34 may be formed using a burr hole forming tool configured to drill, cut or otherwise form the burr hole 34 through the patient's skull 14. An exemplary burr hole forming tool may include a drill. According to some embodiments, the burr hole forming tool (e.g., the drill) is also formed of MRI-compatible material(s). A burr hole ring 36 (FIG. 13) can be mounted about the burr hole 34 to prepare the patient's head 10 for a surgical procedure.

Driver shanks (e.g., the driver shank 110) and cutting heads (e.g., the cutting head 150) can be used with handles of other types and configurations in accordance with further embodiments of the present invention. For example, while the lower handle member 130 is described herein as independently rotatable with respect to the upper handle member 140, according to some embodiments, the upper and lower handle members 130, 140 may be fixed or of a one-piece or unitary construction so that they are not rotatable with respect to one another.

Figure 14:
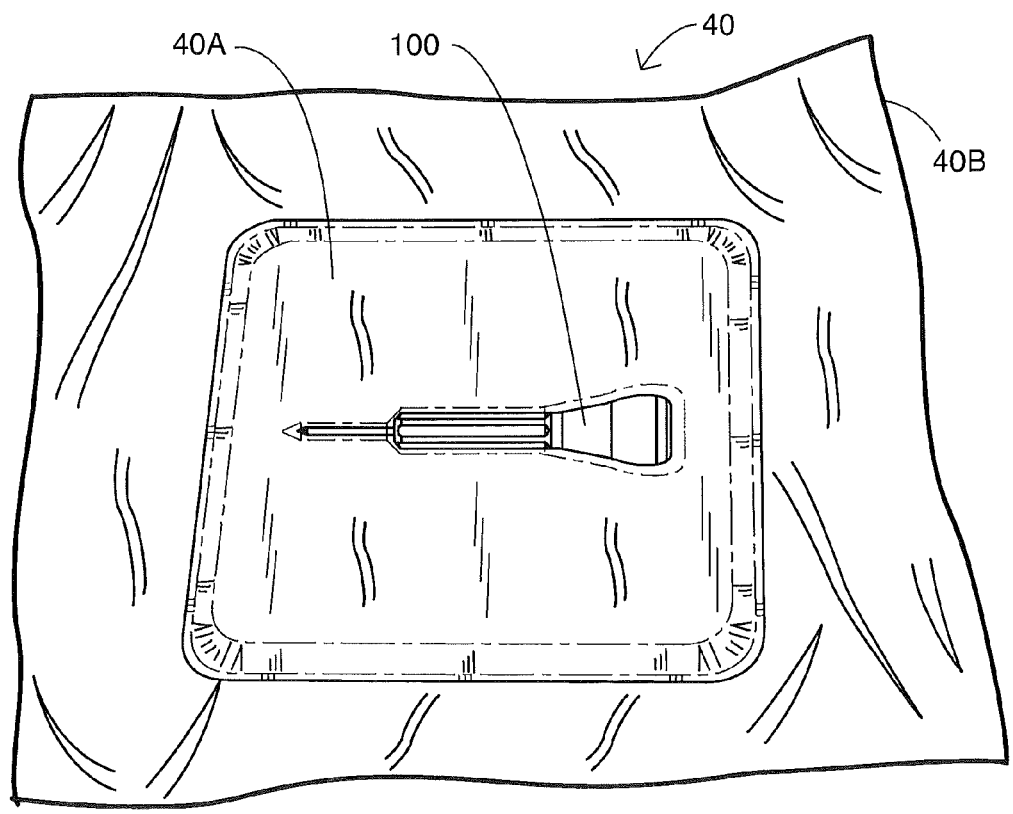
FIG. 14 is a perspective view of a medical kit including the marking tool of FIG. 1.

According to some embodiments and as shown in FIG. 14, the marking tool 100 is packaged in sterile packaging 40 to provide a medical kit. The packaging 40 may include an inner packaging 40A (e.g., a semi-rigid and/or vacuum formed polymeric packaging) and an outer packaging 40B (e.g., a loose, breathable polymeric bag). According to some embodiments, the marking tool 100 is packaged together with the burr hole ring 36, a burr hole forming tool, and/or one or more fiducial markers in the sterile packaging 40 and to form the medical kit.

In some embodiments, the marking tool 100 and methods form a part of or operate with MRI compatible interventional systems. An MRI apparatus may be used to determine the desired location to be marked on the patient using the marking tool 100. In some embodiments, the MRI compatible interventional systems include trajectory guide systems and/or apparatus and related components and methods. According to some embodiments, the trajectory guide apparatus and methods are frameless stereotactic trajectory guide apparatus that may be particularly suitable for deep brain interventional procedures, but may be used in other target anatomical locations as well.

Some embodiments of the invention are directed to MRI interventional procedures and provide interventional tools and/or therapies that may be used to locally place surgical interventional objects, tools or therapies in vivo to site specific regions using an MRI system. The interventional tools can be used to define an MRI-guided trajectory or access path to an in vivo treatment site.

In some embodiments, MRI can be used to visualize (and/or locate) a therapeutic region of interest inside the brain and utilize an MRI to visualize (and/or locate) an interventional tool or tools that will be used to deliver therapy and/or to place a permanently implanted device that will deliver therapy. Then, using the imaging data produced by the MRI system regarding the location of the therapeutic region of interest and the location of the interventional tool, the system and/or physician can make positional adjustments to the interventional tool so as to align the trajectory of the interventional tool, so that when inserted into the body, the trajectory of the interventional tool will intersect with the therapeutic region of interest. With interventional tool now aligned with the therapeutic region of interest, an interventional probe can be advanced, such as through an open lumen inside of the interventional tool, so that the interventional probe follows the trajectory of the interventional tool and proceeds to the therapeutic region of interest. The interventional tool and the interventional probe may or may not be part of the same component or structure.

Tools, methods and systems in accordance with the present invention may be used with apparatus and methods as described in one or more of the following patent applications: U.S. Provisional Patent Application No. 60/933,641, filed Jun. 7, 2007; U.S. Provisional Patent Application No. 60/974, 821, filed Sep. 24, 2007; and PCT Application No. PCT/US2006/045752, published as PCT Publication No. WO/2007064739 A2, and U.S. patent application Ser. No.

12/134,412, filed Jun. 6, 2008, the disclosures of which are hereby incorporated by reference.

According to some embodiments, instrumentation and equipment are inserted through a targeting cannula to execute a diagnostic and/or surgical procedure. According to some embodiments, the procedure includes a deep brain stimulation procedure wherein one or more electrical leads are implanted in a patient's brain. The apparatus described herein can serve to designate an entry point into a patient for an established trajectory for installing the lead or leads or other interventional devices such as, for example, but not limited to, ablation probes, injection catheters and the like.

Some embodiments can be configured to deliver tools or therapies that stimulate a desired region of the sympathetic nerve chain. Other uses inside or outside the brain include stem cell placement, gene therapy or drug delivery for treating physiological conditions. Some embodiments can be used to treat tumors.

In some embodiments, the interventional tools can be configured to facilitate high resolution imaging via integral imaging coils (receive antennas), and/or the interventional tools can be configured to stimulate local tissue, which can facilitate confirmation of proper location by generating a physiologic feedback (observed physical reaction or via fMRI).

Some embodiments can be used to deliver bions, stem cells or other target cells to site-specific regions in the body, such as neurological target and the like. In some embodiments, the systems deliver stem cells and/or other cardio-rebuilding cells or products into cardiac tissue, such as a heart wall via a minimally invasive MRI guided procedure, while the heart is beating (i.e., not requiring a non-beating heart with the patient on a heart-lung machine). Examples of known stimulation treatments and/or target body regions are described in U.S. Pat. Nos. 6,708,064; 6,438,423; 6,356,786; 6,526,318; 6,405,079; 6,167,311; 6,539,263; 6,609,030 and 6,050,992, the contents of which are hereby incorporated by reference as if recited in full herein.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention. Therefore, it is to be understood that the foregoing is illustrative of the present invention and is not to be construed as limited to the specific embodiments disclosed, and that modifications to the disclosed embodiments, as well as other embodiments, are intended to be included within the scope of the invention.

That which is claimed is:

1. A surgical marking tool for marking a location on a patient, the marking tool comprising:
  a cutting head including a screw thread; and
  a handle coupled to the cutting head to rotate the cutting head;
  wherein the screw thread is configured to progressively embed in the patient to mark the location when the cutting head is placed in contact with the patient and rotated with respect to the patient using the handle;
  wherein the marking tool is a burr hole marking tool;
  wherein the screw thread includes a self tapping screw thread configured to self tap into a human skull; and
  wherein the cutting head has a sharp leading end section configured to easily pierce through a respective patient's scalp;
  wherein the marking tool includes a cutting flute defined in the leading end section and defining a collection pocket within the cutting head to collect material through which the cutting head is driven, the cutting flute having a cutting face having a sharp cutting edge.

2. The marking tool of claim 1 wherein the cutting head has a lead end and a limiter feature spaced apart a distance from the lead end, and an axial boring length extending from the lead end to a proximal end of the limiter feature is less than a thickness of the patient's skull.

3. The marking tool of claim 2 wherein the axial boring length is in the range of from about 2.5 mm to 7 mm.

4. The marking tool of claim 1 wherein:
  the handle includes first and second handle members that cooperate and are rotatable with respect to one another; and
  the cutting head is affixed to the first handle member for rotation therewith.

5. The marking tool of claim 4 wherein:
  the first handle member is a lower handle member and the second handle member is an upper handle member; and
  the upper handle member is configured and positioned to be held by a user's hand while the user rotates the cutting head using the lower handle member.

6. The marking tool of claim 5 wherein the upper handle member has an upper end portion with a bulbous shape.

7. The marking tool of claim 6 wherein the lower handle member includes flutes.

8. The marking tool of claim 1 wherein the marking tool is constructed entirely of MRI-compatible material or materials.

9. The marking tool of claim 1 wherein the self tapping screw thread is configured to form a thread in the patient's skull corresponding to the self tapping screw thread when the self tapping screw thread is rotated into the patient.

10. The marking tool of claim 9 wherein the self tapping screw thread is configured to be progressively removed from the patient's skull by counter-rotating the self tapping screw thread with respect to the patient.

11. The marking tool of claim 1 wherein the self tapping screw thread extends substantially fully to a sharp leading tip of the sharp leading end section.

12. The marking tool of claim 1 including a driver shank coupling the cutting head to the handle, wherein the cutting head is affixed to the driver shank.

13. The marking tool of claim 1 including a driver shank coupling the cutting head to the handle, wherein the cutting head is integrally formed with the driver shank.

14. The marking tool of claim 1 wherein the self tapping screw thread has a tapered major diameter increasing in diameter in a direction from the sharp leading end section to the handle.

15. A surgical marking tool for marking a location on a patient, the marking tool comprising:
  a driver shank;
  a cutting head affixed to or integrally formed with the driver shank, the cutting head including a screw thread; and
  a handle coupled to the cutting head by the driver shank to rotate the cutting head;
  wherein the screw thread is configured to progressively embed in the patient to mark a location when the cutting head is placed in contact with the patient and rotated with respect to the patient using the handle;
  wherein the marking tool includes a cutting flute defined in a leading end section and defining a collection pocket within the cutting head to collect material through which the cutting head is driven, the cutting flute having a cutting face having a sharp cutting edge.

16. The marking tool of claim 15 wherein the cutting head is integrally formed with the driver shank.

* * * * *